United States Patent [19]

Sessler et al.

[11] Patent Number: 5,270,214
[45] Date of Patent: Dec. 14, 1993

[54] METHOD FOR SEQUENCING DNA BASE PAIRS

[75] Inventors: Andrew M. Sessler, Oakland; John Dawson, Pacific Palisades, both of Calif.

[73] Assignee: The United States of America as represented by the United States Department of Energy, Washington, D.C.

[21] Appl. No.: 530,693

[22] Filed: May 30, 1990

[51] Int. Cl.$^5$ .................. G01N 33/48; G01N 25/18
[52] U.S. Cl. ................................ 436/94; 436/149; 250/340; 250/341
[58] Field of Search ............ 435/6, 289, 291, 820; 436/501, 94; 935/77, 78

[56] References Cited

U.S. PATENT DOCUMENTS

| | | | |
|---|---|---|---|
| 4,675,283 | 6/1987 | Roninson | 435/6 |
| 4,706,192 | 11/1987 | Nasu | 364/413 |
| 4,729,947 | 3/1988 | Middendorf | 435/6 |
| 4,802,101 | 1/1989 | Hara | 364/496 |
| 4,865,968 | 12/1989 | Orgel | 435/6 |
| 5,003,815 | 4/1991 | Martin et al. | 250/306 |

OTHER PUBLICATIONS

Allinger et al., "Organic Chemistry", Worth Publishers, Inc., NY, NY, 1971.
Dunlap et al., Nature 342:204-206 (Nov. 1989).
Keller et al., PNAS, USA 86:5356-5360 (Jul. 1989).
J. Dawson and A. Sessler, "DNA Base Sequencer: Scanning Tunneling Microscope Plus Infrared Radiation," Lawrence Berkeley Laboratory Report LBL-27660, Aug. 1989, pp. 108-113.
Charles Petit, "Beyond the Cutting Edge," MOSAIC, vol. 20, No. 2, Summer 1989, pp. 24-35.
Thomas P. Beebe, Jr., "Direct Observation of Native DNA Structures with the Scanning Tunneling Microscope," Science, vol. 243, Jan. 20, 1989, pp. 370-372.

Primary Examiner—Robert A. Wax
Assistant Examiner—Stephanie W. Zitomer
Attorney, Agent, or Firm—Isabelle R. McAndrews; Roger S. Gaither; William R. Moser

[57] ABSTRACT

The base pairs of a DNA structure are sequenced with the use of a scanning tunneling microscope (STM). The DNA structure is scanned by the STM probe tip, and, as it is being scanned, the DNA structure is separately subjected to a sequence of infrared radiation from four different sources, each source being selected to preferentially excite one of the four different bases in the DNA structure. Each particular base being scanned is subjected to such sequence of infrared radiation from the four different sources as that particular base is being scanned. The DNA structure as a whole is separately imaged for each subjection thereof to radiation from one only of each source.

1 Claim, 2 Drawing Sheets

Adenine

Guanine

Cytosine

Thymine

METHOD FOR SEQUENCING DNA BASE PAIRS

BACKGROUND OF THE INVENTION

The United States Government has rights to this invention pursuant to Contract No. DE-AC03-76SF00098 between the U. S. Department of Energy and the University of California.

This invention relates to the sequencing of base pairs of the strands of a DNA molecule.

The gene of an organism is made up of deoxyribonucleic acid (DNA) in which four kinds of organic bases are arranged in pairs along a double helix structure. The four kinds of bases are adenine (A), guanine (G), cytosine (C), and thymine (T). In order to obtain specific genetic information, it is essential to determine the particular sequence of the base pairs along the structure.

Present methods of sequencing base pairs use chemical methods of isolating the base pairs and then identifying them. This is a tedious and time-consuming task. At present, it is estimated that the position of one base pair of a DNA structure can be determined every three minutes. However, since there are approximately six billion base pairs on human DNA, it would take 34,000 years to completely map the entire human genome at this pace.

It has also been proposed that the sequencing can be done by X-ray imaging. However, the necessary resolution requires X-rays of a few Kev. Such energetic photons are efficient at photo ionizing K shell and other tightly-bound electrons. This will produce highly energetic and reactive atoms in the molecule which almost certainly will cause severe damage. The ratio of elastic scattering to photo ionization is such that the X-ray flux required to make an image will probably completely destroy DNA.

The advent of the scanning tunneling microscope (STM) has brought a powerful new tool to the study of the molecular and atomic structure of materials, and has enabled precise pictures of atoms and molecules to be imaged. In general, an STM has an extremely fine probe tip which is positioned at a very close distance (in the order of angstroms) from the surface of the specimen under consideration. A phenomenon known as quantum tunneling will take place with tunneling current flowing through the insulation (vacuum, liquid or even air) between the specimen surface and the tip. Tunneling is extremely sensitive. Decreasing the gap between the specimen surface and tip by a single angstrom can increase tunneling current by an order of magnitude.

The STM probe tip is moved back and forth and from side to side of a chosen area to scan the structure within that area. The topography of the surface of the structure is measured in either of two modes: constant height or constant current. In the first, the controls skim the tip through the area while maintaining it at a constant height and re-create the topography from recorded variations in the tunneling current. In the second, a feedback circuit adjusts the altitude to keep the tunneling current constant, with the altimeter data being the basis for the produced image. In either mode, raw data are typically a series of irregular scan lines rendered by computed averaging and smoothing methods into images, usually displayed on video screens, that highlight chosen features, often with photograph-like clarity. STM images can have magnifications of 100 million or more, and can routinely resolve features smaller than a single angstrom (atoms are about two or three angstroms across).

As described by T. P. Beebe, et al., "Direct Observations of Native DNA Structures with the Scanning Tunneling Microscope," *Science*, Jan. 20, 1989, pages 370-372, the STM has been used to image double-stranded DNA. Although there are many questions about the interpretation of the particular DNA images shown in the article, it does appear that the STM can be of considerable use in the investigation of DNA.

SUMMARY OF THE INVENTION

It is a primary object of the invention to provide a method of sequencing base pairs of DNA which is rapid, accurate and nondestructive of the molecule.

Additional objects, advantages, and novel features will be set forth in the description which follows, and in part will become apparent to those skilled in the art upon To achieve the foregoing and other objectives, and in accordance with the present invention, as described and broadly claimed herein, an improved method is provided for analyzing a molecular structure having a plurality of groups of atoms in which there are at least two different kinds of groups of atoms with each of the different kinds of groups of atoms being excitable by the absorption of electromagnetic radiation applied thereto of a particular frequency which is different for each different kind of groups of atoms, wherein the individual groups of the plurality of groups of atoms are scanned sequentially by the probe tip of a scanning tunneling microscope, and wherein each of the scanned groups of atoms is sequentially subjected to electromagnetic radiation of each of the different frequencies which will cause each different kind of groups of atoms to be excited during the time that the group of atoms is being scanned by the probe tip.

A more specific aspect of the invention is that the bases in a DNA specimen are scanned and that the DNA specimen is sequentially subjected, during scanning, to infrared electromagnetic radiation of four different frequencies, each frequency being selected to excite preferentially a different one of the four bases in a DNA molecule.

DESCRIPTION OF THE PREFERRED EMBODIMENT

Figure 1:
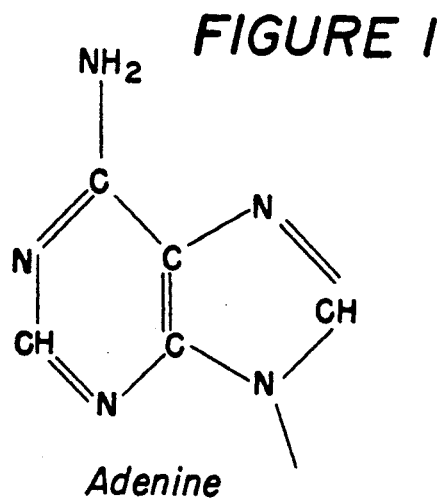
FIGS. 1-4 illustrate the structures of the four DNA bases, adenine, guanine, cytosine, and thymine.
Figure 2:
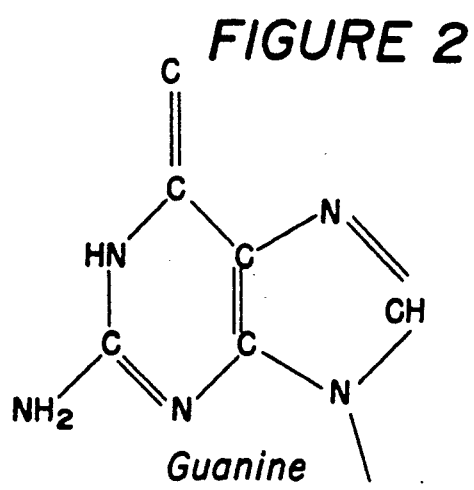
Figure 3:
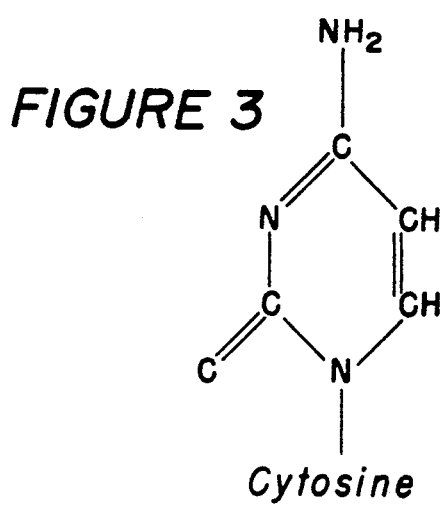
Figure 4:
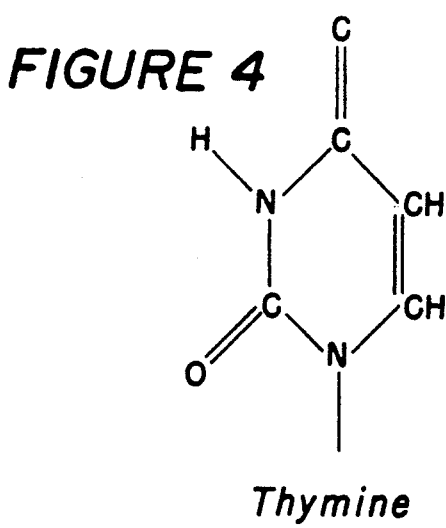
Figure 5:
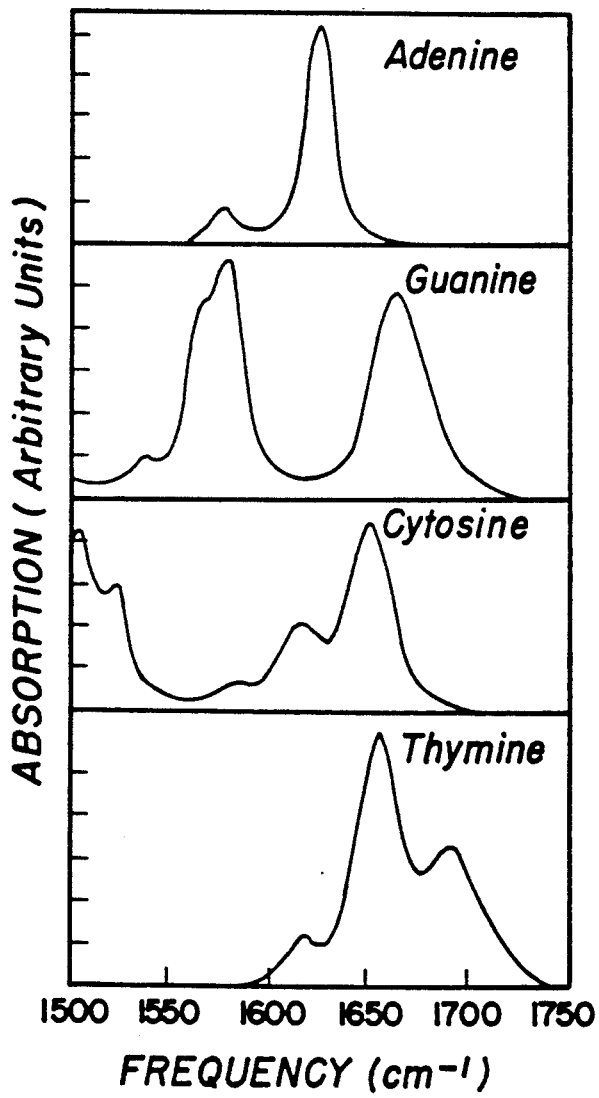
FIG. 5 illustrates the infrared absorption spectrum of the four DNA bases, in arbitrary units of absorption.

Referring now to the drawings, wherein a preferred embodiment of the invention is illustrated, FIGS. 1-4 show that the four different bases in a DNA molecule constitute four different groups of atoms each having quite different vibrational atomic structures. As seen there, thymine is shown in FIG. 4 as having a unique imide substructure. The characteristic exocyclic amine at C-6 in cytosine is shown in FIG. 3 (different from that of adenine and guanine), and FIG. 2 shows guanine having a unique amide-like NH in Position 1. Adenine does not have any unique functional groups, but the exocyclic amine is in a somewhat different chemical environment than either guanine or cytosine and, as a result, absorbs at a somewhat different infrared frequency. The infrared absorption spectra are shown in FIG. 5. It can be seen that preferential excitation of the different bases is possible.

Figure 6:
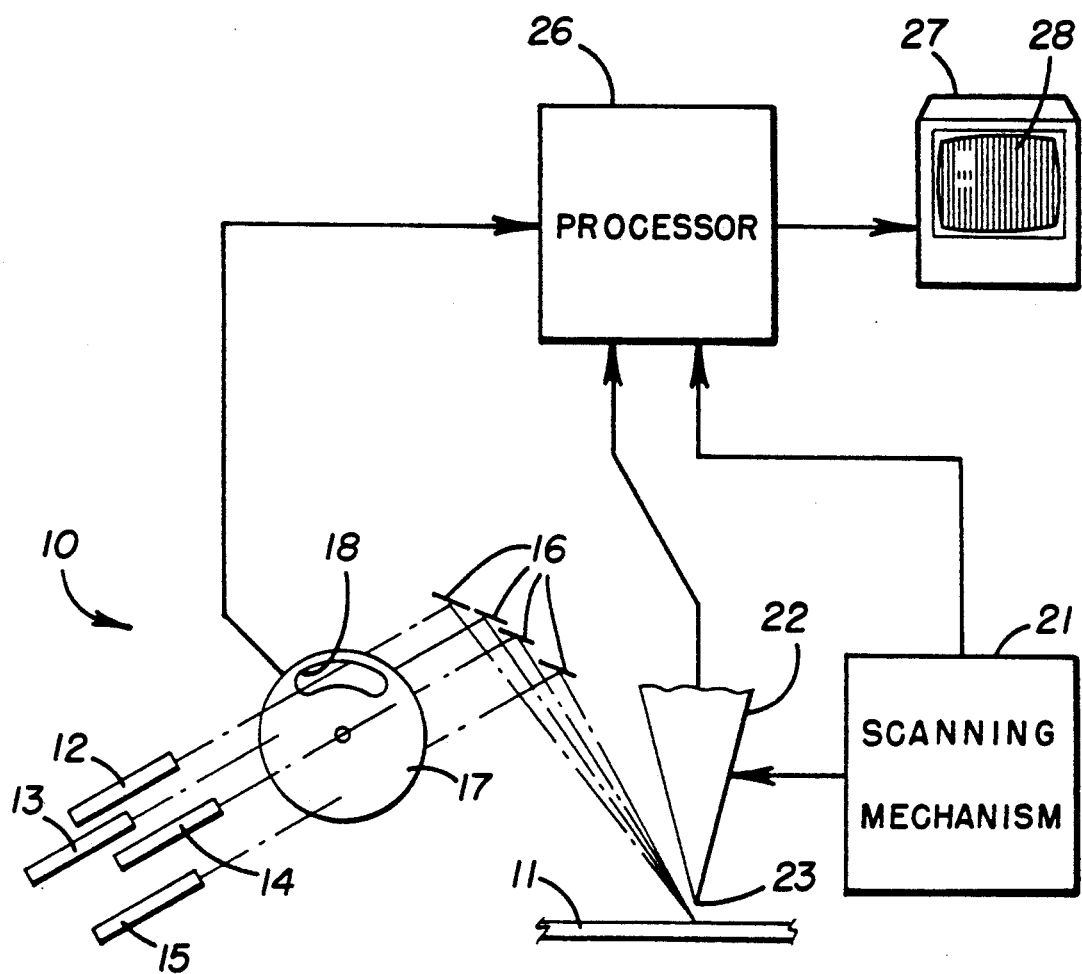
FIG. 6 is a schematic illustration of a system for sequencing base pairs of DNA structure.

FIG. 6 illustrates a system 10 for sequencing the base pairs of a DNA molecules. A DNA specimen is prepared in a known manner and deposited on a suitable substrate 11, such as a freshly cleaved, highly ordered pyrolytic graphite substrate. For example, the procedure discussed in the previously mentioned article from science may be used for this purpose.

A relatively large area (e.g., 100×100 microns) on the substrate, with a DNA specimen within the area, is then irradiated with infrared radiation from four different laser sources 12, 13, 14, and 15 whose radiation is directed by mirrors 16 to the desired, area on the substrate. The spectral emission (i.e. the frequency of electromagnetic radiation) of each of the laser sources is selected to preferentially excite a different one of the four bases in the DNA specimen. A rotatable disk 17 is disposed between mirrors 16 and the laser sources, disk 17 being opaque to infrared radiation and having an aperture 18 which will sequentially allow one only of the four beams to pass therethrough as the disk rotates.

A suitable scanning mechanism 21 will cause the STM probe 22 to move so that its tip 23 will sequentially scan the bases of the DNA specimen in the irradiated area. The rate of rotation of disk 17 is coordinated with the rate of scanning movement of probe tip 23 so that the DNA structure will be irradiated sequentially by all four of the laser sources while each single base is being scanned by the probe tip.

When the particular base under the probe tip is subjected to the particular laser beam matching its absorption characteristics, the base will be excited and will resonate. The dimension of the excited base will expand and contract with the vibration, and as a result, the distance to the STM tip 23 will vary periodically. Because the tunneling current varies exponentially with the distance from the surface being observed and the STM tip, the average current will vary in accordance with the degree of excitation. As mentioned previously, the tunneling current increases by a factor of 10 for every angstrom decrease in sample-tip separation. With an excitation of the base which reduces the minimum separation by 0.04 angstrom, the average current will increase by 10%.

The entire portion of the DNA specimen under consideration is scanned, with each base in the specimen being irradiated sequentially by each one of four laser beams, so that one of these beams will cause that base to resonate while it is being scanned.

During the scanning, the processor 26 receives information: from the probe tip 23 proportional to the instantaneous amount of tunneling current; from the scanning mechanism 21 indicative of the instantaneous position of the tip 23 during its scan; and from the rotating disk 18 indicative of the particular laser source which is irradiating the specimen area at any instant. When the scan is complete, the tunneling current information is processed by known averaging and smoothing methods and is available to the imager 27 for displaying on the screen 28.

The atomic structure of the scanned portion of the DNA specimen is then imaged separately for each irradiation thereof by one only of the four laser sources, in order to identify the different bases which have been scanned. For example, when the DNA structure is imaged during irradiation thereof by the laser which causes excitation of the cytosine bases the image will show all of the cytosine bases as visually different than in the other three images of the scanned atomic structure when irradiated by each of the other three laser sources. In like manner, the other bases in the DNA specimens can be identified by the particular image in which they are excited.

The sequencing method described above is much cheaper, easier, and faster than heretofore. An STM tip will typically scan at a rate of about 1,000 angstrom per second, and hence one instrument can sequence at a rate of about 30 base pairs per second. Further, the method is nondestructive to the specimens being observed.

The foregoing description of the preferred embodiment has been presented for the purposes of illustration and description. The embodiment was chosen in order to further explain the principles of the invention and its practical applications, thereby enabling others in the art to most effectively the use invention in various other embodiments and with various other modifications as may be suited to the particular use contemplated. It is not intended to be exhaustive or to limit the invention to the precise embodiment described.

Obviously, many other modifications are possible in light of the above teaching. For example, the invention can be used to study other specimens, inert substances as well as a range of organic samples, having at least two components with different vibrational characteristics which may be preferentially excited by different stimuli. Moreover, the stimuli need not be infrared radiation. Energy can be transferred from electronic excitation into vibrational modes or if electronic excitation remains localized sufficiently well, they might produce image discrimination. It is intended that the scope of the invention be defined by the claims appended hereto.

We claim:

1. A method of sequencing the base pairs of a DNA molecule utilizing a scanning tunneling microscope, comprising the steps of:

disposing at least a portion of said DNA molecule in a position to be scanned by a probe tip of said scanning tunneling microscope which DNA molecule has four different bases;

sequentially irradiating said portion of said DNA molecule with infrared radiation of four different frequencies, each of said four different frequencies being selected to excite preferentially a different one of the four bases of said DNA molecule, with each base of said portion of said DNA molecule being subjected sequentially to all of said different frequencies of said radiation while that particular base is being scanned;

imaging said irradiated portion of said DNA molecule each time said DNA molecule is irradiated with a different one of said different frequencies for identifying said four bases to thereby obtain the sequence of the DNA molecule.

* * * * *